United States Patent
Fleischhacker et al.

(10) Patent No.: US 9,387,323 B2
(45) Date of Patent: Jul. 12, 2016

(54) GUIDEWIRE-STYLE PACING LEAD

(75) Inventors: Mark G. Fleischhacker, Minnetonka, MN (US); Joseph F. Fleischhacker, Mound, MN (US)

(73) Assignee: Lake Region Manufacturing, Inc., Chaska, MN (US)

( * ) Notice: Subject to any disclaimer, the term of this patent is extended or adjusted under 35 U.S.C. 154(b) by 8 days.

(21) Appl. No.: 12/887,871

(22) Filed: Sep. 22, 2010

(65) Prior Publication Data

US 2011/0071608 A1 Mar. 24, 2011

Related U.S. Application Data

(60) Provisional application No. 61/245,117, filed on Sep. 23, 2009.

(51) Int. Cl.
| | | |
|---|---|---|
| *A61N 1/05* | (2006.01) | |
| *A61M 25/01* | (2006.01) | |
| *A61M 25/09* | (2006.01) | |

(52) U.S. Cl.
CPC ...... *A61N 1/056* (2013.01); *A61M 2025/09066* (2013.01); *A61M 2025/09083* (2013.01); *A61M 2025/09183* (2013.01)

(58) Field of Classification Search
CPC ....... A61N 1/05; A61N 1/056; A61N 1/0563; A61N 1/0587; A61N 1/0595; A61N 2001/0585; A61M 2025/09066; A61M 2025/09083; A61M 2025/09183
USPC ................. 607/115–119, 122–126
See application file for complete search history.

(56) References Cited

U.S. PATENT DOCUMENTS

| | | | | |
|---|---|---|---|---|
| 4,317,459 A | * | 3/1982 | Gilman | 607/126 |
| 4,338,947 A | | 7/1982 | Williams | |
| 4,437,474 A | * | 3/1984 | Peers-Trevarton | A61N 1/056 29/605 |
| 4,475,560 A | | 10/1984 | Tarjun et al. | |
| 4,530,368 A | | 7/1985 | Saulson et al. | |
| 4,541,440 A | | 9/1985 | Parsonnet | |
| 4,602,645 A | | 7/1986 | Barrington et al. | |
| 4,972,848 A | * | 11/1990 | Di Domenico et al. | 607/127 |
| 5,154,705 A | | 10/1992 | Fleischhacker et al. | |
| 5,354,327 A | | 10/1994 | Smits | |
| 5,824,030 A | * | 10/1998 | Yang et al. | 607/122 |
| 5,851,226 A | | 12/1998 | Skubitz et al. | |
| 5,978,705 A | | 11/1999 | Kenknight et al. | |
| 6,161,029 A | | 12/2000 | Spreigl et al. | |
| 6,400,992 B1 | * | 6/2002 | Borgersen et al. | 607/122 |

(Continued)

FOREIGN PATENT DOCUMENTS

| | | |
|---|---|---|
| JP | H06-49701 | 3/1993 |
| WO | WO2009046274 | 4/2009 |
| WO | 2011037978 A2 | 3/2011 |

OTHER PUBLICATIONS

Hara, H., "Percutaneous Ballon Aortic Valvuloplasty revisited", Circulation, 2007; 115:e334-e338.

(Continued)

*Primary Examiner* — Allen Porter, Jr.
(74) *Attorney, Agent, or Firm* — Michael F. Scalise; Grady J. Frenchick (57) ABSTRACT

The present invention relates generally to implantable pacing leads, and more particularly to guidewire-styled temporary transvenous endocardial leads for pacing or other medical applications.

21 Claims, 8 Drawing Sheets

(56) References Cited

U.S. PATENT DOCUMENTS

| | | | |
|---|---|---|---|
| 6,408,213 B1 | 6/2002 | Bartig et al. | |
| 6,968,237 B2* | 11/2005 | Doan et al. | 607/122 |
| 6,978,185 B2* | 12/2005 | Osypka | 607/122 |
| 7,225,035 B2* | 5/2007 | Brabec et al. | 607/122 |
| 7,627,382 B2 | 12/2009 | Minar et al. | |
| 2001/0018607 A1 | 8/2001 | Borgersen et al. | |
| 2002/0098307 A1 | 7/2002 | Schwartz et al. | |
| 2003/0023294 A1* | 1/2003 | Krall | A61N 1/0563 607/122 |
| 2003/0109914 A1 | 6/2003 | Westlund et al. | |
| 2004/0064172 A1 | 4/2004 | Mcvenes et al. | |
| 2004/0064173 A1 | 4/2004 | Hine et al. | |
| 2004/0088034 A1* | 5/2004 | Smits et al. | 607/122 |
| 2004/0116993 A1* | 6/2004 | Clemens | A61N 1/056 607/122 |
| 2004/0215300 A1* | 10/2004 | Verness | A61N 1/056 607/116 |
| 2005/0075662 A1 | 4/2005 | Pedersen et al. | |
| 2005/0090846 A1 | 4/2005 | Pedersen et al. | |
| 2006/0037195 A1 | 2/2006 | Bauer et al. | |
| 2007/0088355 A9 | 4/2007 | Auth et al. | |
| 2007/0185556 A1* | 8/2007 | Williams | A61N 1/056 607/116 |
| 2007/0250144 A1 | 10/2007 | Falk et al. | |
| 2007/0299493 A1* | 12/2007 | Osypka | 607/127 |
| 2008/0033497 A1* | 2/2008 | Bulkes et al. | 607/9 |
| 2008/0242976 A1 | 10/2008 | Robertson et al. | |
| 2008/0262584 A1* | 10/2008 | Bottomley et al. | 607/119 |
| 2009/0018608 A1 | 1/2009 | Schwartz et al. | |
| 2009/0157136 A1 | 6/2009 | Yang et al. | |
| 2010/0137954 A1* | 6/2010 | Seifert | A61N 1/056 607/115 |
| 2011/0093054 A1* | 4/2011 | Ameri | A61N 1/0563 607/122 |

OTHER PUBLICATIONS

International Search Report and Written opinion for PCT App. No. PCT/US2010/049789 mailed on Jun. 20, 2011.

Extended EP Search Report for EP Pat. App. No. 10819375.6 mailed on Feb. 11, 2013.

* cited by examiner

GUIDEWIRE-STYLE PACING LEAD

CROSS REFERENCE TO RELATED APPLICATIONS

This application is a nonprovisional of application Ser. No. 61/245,117 which was filed on Sep. 23, 2009, the disclosure of which is incorporated by reference herein in its entirety.

FIELD OF INVENTION

The present invention relates generally to implantable pacing leads, and more particularly to guidewire-styled temporary transvenous endocardial leads for pacing or other medical applications.

BACKGROUND

Endocardial pacing leads may be classified in two broad categories: permanent pacing leads and temporary pacing leads. Permanent and temporary pacing leads are generally characterized in having different physical structures, materials and configurations. Structural differences between the two general types of pacing leads are driven primarily by cost considerations and the different natures of the applications for which the two types of leads are employed. Most temporary pacing leads are used for one week or less and then disposed of, while permanent pacing leads often remain implanted and functioning in patients for five years or longer.

When a permanent pacing lead is implanted in a patient, a pacemaker and an electrical connection between the pacing lead and the pacemaker are generally embedded within the body. Permanent pacing leads are commonly implanted with the aid of stylets that increase the speed and accuracy of lead electrode placement. Moreover, once the lead has been implanted and the stylet withdrawn, the remaining lead body becomes flexible and does not retain the stiffness imparted by the stylet. Thus, stylets are highly desirable and often used in permanent leads.

When implanting a permanent pacing lead, a peripheral vein such as the left or right subclavian vein is punctured by an introducer through an incised portion of the skin. A prior art "catheter" or a lead containing a stylet is inserted through the introducer. When a prior art catheter is used, the catheter's distal end is held at the apex of the right ventricle or right atrium while a temporary lead is inserted through the prior art catheter until the distal end of the lead engages and is lodged or otherwise affixed to the endocardium of the right ventricle or right atrium; the prior art catheter is then withdrawn. If a lead having a stylet is used, the distal end of the lead is guided to the apex of the right ventricle or the atrial appendage in the atrium, the lead electrode tip is affixed to the endocardium and the stylet is removed.

Temporary transvenous endocardial pacing leads are generally used prior to pacemaker implant surgery or in emergency treatment of heart arrhythmias and myocardial infarction. In temporary pacing, the distal end of a temporary pacing lead is inserted transvenously in the body using some of the techniques described above for permanent leads while the proximal end is located outside the body where electrical and mechanical connections to an external temporary pacemaker are made. The temporary pacemaker coupled to the temporary lead provides pulses of electrical energy to stimulate the endocardium through the temporary pacing lead. Typically, the temporary pacing lead is extricated from the patient when a permanent, implantable pacemaker and corresponding permanent lead are implanted, or when the need for temporary pacing no longer exists.

Epicardial pacing leads are often used in temporary pacing applications following transthoracic surgery, where the electrode is affixed to the surface of the heart. It is an advantage of endocardial leads that they typically require lower stimulation thresholds to pace the heart than those required with epicardial leads because endocardial leads provide lower stimulation thresholds over time. Temporary pacing leads should not be reused, are designed to be disposed of after a single use, and are not designed for use over prolonged periods of time.

Some ideal attributes of temporary pacing leads include: (1) small lead diameter; (2) secure placement of the tip electrode in the selected heart chamber; (3) high degree of steerability, control and torque transfer during implantation; (4) minimal damage to vein, heart valve and endocardial tissue during implantation; (5) reliable conduction of electrical impulses during use; (6) easy removal from the heart chamber with minimum tissue damage, and (7) low cost.

Secure placement of the tip electrode in the selected heart chamber is required to assure appropriate and reliable depolarization or "capture" of cardiac tissue by electrical stimuli delivered by the pacemaker or pulse generator. Known temporary transvenous leads suffer from a relatively high rate of dislodgment from sites adjacent to or on the endocardium. This is not surprising in view of the fact that no prior art temporary transvenous pacing leads utilize active fixation devices to positively secure the electrode tip to the endocardium. Instead, known temporary pacing leads rely on force provided by a bent or curved lead body as a means of pushing the distal electrode tip against endocardial tissue. If the pacing lead body or tip shifts position as a result, for example, of patient postural changes, the tip electrode may disengage or float away from the endocardium. This, in turn, may result in a loss of capture, or in a reduction of the degree of electrical coupling between the electrode and endocardium.

It is desirable that leads particularly temporary pacing leads have a high degree of steerability, control and torque transfer to permit relatively quick and accurate placement of the electrode tip at the desired site within the heart, and the initiation of temporary pacing with minimum delay and tissue trauma. Speed and accuracy of lead placement become especially important when attempting to restore a patient's heartbeat under emergency conditions. In the past, there have been a limited number of sites in the atrium and ventricle where lead placement could be effected. The accuracy of where the pacing lead is placed in the atrium or ventricle thus assumes considerable importance.

Ideally, temporary pacing leads should cause no damage to vein, heart valve and cardiac tissue during implantation. The temporary lead should have a highly flexible and soft distal tip that readily follows the direction of venous blood flow. Such directional following is often referred to as "floating" the lead or catheter through the venous system. A soft flexible distal tip on the lead or catheter may help prevent trauma to the surrounding venous and cardiac tissues as the lead is directed to the fixation site.

Temporary pacing leads should reliably conduct electrical pulses from the pacemaker even when sutures at the lead anchor suture site are drawn too tight, the lead is stressed by excessive patient movement, or when the pacemaker or attached lead is subjected to rough handling by hospital personnel. Temporary pacing leads are generally designed for a single use over a limited duration of time, and therefore are typically not constructed of materials that are as biostable, durable, strong or robust as those used in permanent pacing leads.

The technology and medicine of Implantable pacing leads, particularly temporary implantable pacing leads, are extensively discussed in U.S. Pat. No. 5,851,226 to Skubitz et al., "Temporary Transvenous Endocardial Lead" the entirety of which is incorporated by reference herein. Of particular relevance for background information regarding this invention is the disclosure of Skubitz et al. starting a column 1, line 1 through column 6 line 55, (including the Prior Art Patents listed in TABLE 1 in column 6), the disclosures of which is specifically incorporated by reference herein and is the basis for much of the discussion above.

Other disclosures incorporated by reference herein in their entireties for their background disclosures and filed as part of this application include the following:

Saulson et al., U.S. Pat. No. 4,530,368 "Temporary Bipolar Pacing Lead";
Tarjan et al., U.S. Pat. No. 4,475,560, "Temporary Pacing Lead Assembly";
Parsonnet, U.S. Pat. No. 4,541,440, "Bipolar Epicardial Temporary Pacing Lead";
Barrington et al., U.S. Pat. No. 4,602,645, Atrio-Ventricular Pacing Catheter";
Williams, U.S. Pat. No. 4,338,947, "Positive Fixation Heart Wire"

The terms "temporary pacing lead" and "temporary lead" mean, for example, a low cost, implantable, percutaneously introduced, transvenous, endocardial lead having at least one electrode for pacing, capturing, cardioverting or defibrillating the heart at or near an endocardial site, the lead being intended for use over a relatively short and limited period of time that is usually several days in length and occasionally as long as about one month, the lead being disposed of after a single use, where the design and structure of, and materials used in, the lead correspond to the foregoing single use and low cost requirements. The terms "temporary pacing lead" and "temporary lead" include within their scopes unipolar and bipolar temporary pacing leads.

The term "active fixation" means the positive fixation of the distal end of a pacing lead, or a portion near the distal end of the pacing lead, to endocardial tissue, or through, propinquant to, or into endocardial tissue.

The term "distal" means that portion of an apparatus, or component or element of an apparatus, which is disposed in closer proximity to the end of the lead or guide catheter that is inserted first inside a patient's body during a lead implantation procedure than it is to the end of the lead or guide catheter that remains outside the patient's body during the lead implantation procedure.

The term "guide catheter" means a catheter that is designed for use in combination or in conjunction with a separate lead body, where the guide catheter forms a tubular shape and accepts the lead body inside a central lumen or tube defined by inner sidewalls, the inner sidewalls providing a bearing or load surface against which the lead body acts when one lead body end is being rotated by a physician.

SUMMARY OF THE INVENTION

Briefly, in one aspect, the present invention is a multi-filar, i.e., 2 filars or more, guidewire-style pacing lead. Leads of this invention may be used temporarily or permanently for tissue, e.g., cardiac tissue, pacing/sensing/defibrillation procedures. Leads of this invention generally comprise at least first and second electrode or contact means insulatively and electrically coupled to the filars, the filars also being coupled to a connector means to permit sensing, pacing, or stimulation of tissue by the use of an appropriately connected electronic device. The contact means of a lead of this invention are generally physically separated so that no "short" electrical pathway (e.g., through tissue rather than the lead itself) is available therebetween. Leads of this invention can, of course, be permanently implanted, particularly with an appropriate stimulation/sensing electronic device.

In one embodiment of this invention the diameters of at least one of the two of the filars are different. In a further embodiment the lead comprises an elongate lead body and is quadrifilar, three of the four filars having one diameter and the fourth having a second larger or smaller diameter.

In a further embodiment of this invention the lead body has a shape or configuration which tends to create or provide a bias or pressure directed toward one or both contact means, structures, or electrodes, the bias being directed toward tissues to be electrically monitored or stimulated.

The present invention relates to guidewire-style or guidewire-based pacemaker leads or pulse generator leads. Defibrillator leads are included. Endocardial and epicardial lead applications are included. Temporary or permanent, unipolar and bipolar pacing/sensing lead applications are contemplated. One skilled in this art will readily appreciate the many structural and method-of-use variations suggested by the present disclosure.

Pacing leads of the present invention are said to be "guidewire-based" or "guidewire-style". By this terminology it is meant that leads of this invention have structural and performance attributes of medical guidewires not normally found in pacing leads. Specifically this terminology means that leads of this invention are proximally steerable, pushable, and torquable as those terms are understood in the guidewire art. Longitudinal and transverse directional control, including up to 1:1 torque transmission distal to proximal ends, are included. These structural and performance attributes permit leads of this invention to navigate and to traverse complex vascular structures generally without the use of collateral instruments such as stylets, guide catheters, or sheaths. It will be appreciated that the features of the present invention brings significant cost and time savings to the many and varied medical procedures in which the present invention can be used.

BRIEF DESCRIPTION OF THE SEVERAL VIEWS OF THE DRAWINGS

The present invention will now be illustrated with reference to the attached FIGS. 1-10, which should be considered as illustrative and not limiting, and in which.

DETAILED DESCRIPTION OF THE INVENTION

The invention is now illustrated in the following disclosure and the attached Figures which are intended to be illustrative and not limiting. It is to be noted that the description herein focuses primarily upon "temporary" pacing leads. That discussion is intended to be illustrative but not limiting of the present invention. Clearly, with minor modifications to the lead structure e.g., providing a suitable coupler for an implantable defibrillator/pulse generator/sensor apparatus and active lead fixation means, (those structural modifications not being part of this invention), appropriate pulse/sense/defibrillator electronics, and most likely, active-fixation means of the present inventive guidewire-style pacing leads could be used for, adapted for, or for both temporary and chronically implanted or "permanent" pacing/sensing/defibrillation applications.

Figure 1:
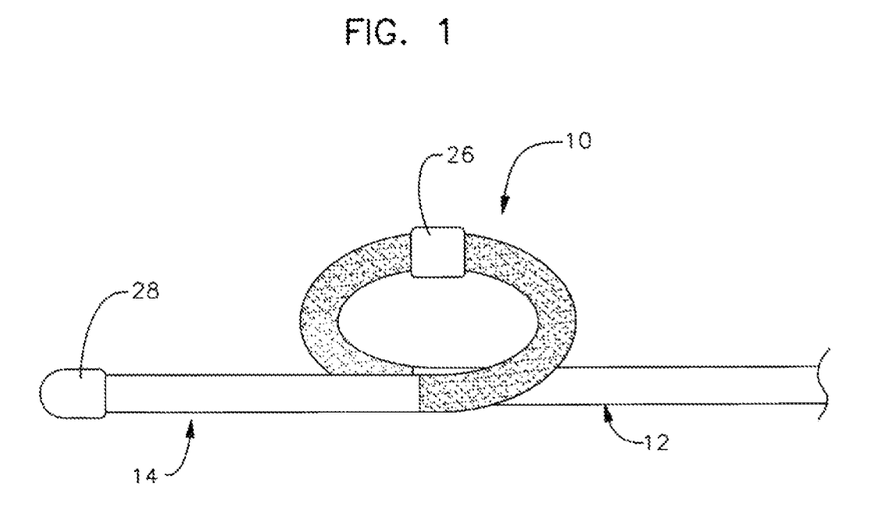
FIGS. 1, 1A and 1B illustrate a coil or "pigtail" version of a temporary pacing lead of the present invention.
Figure 1A:
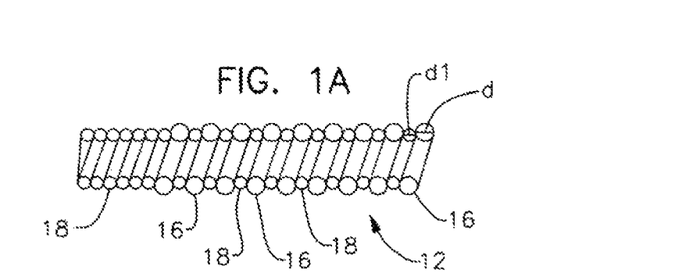
Figure 1B:
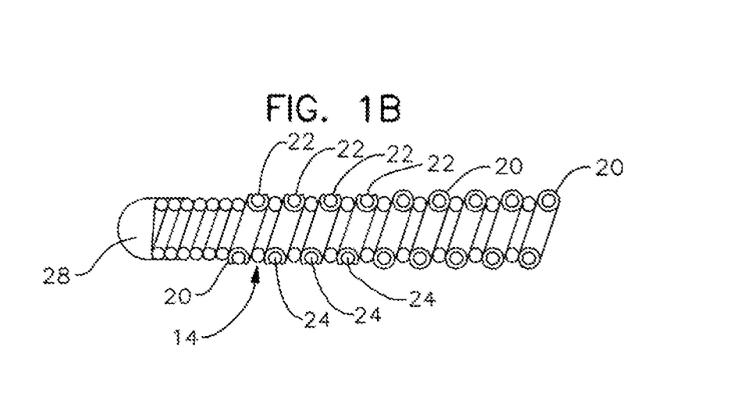

FIGS. 1, 1A, and 1B illustrate a coil or "pig-tail" version of a temporary pacing lead 10 of the present invention. FIG. 1 is a perspective view of this embodiment of the invention while FIGS. 1A and 1B show in section a segment 12 of the elongate or cylindrical guidewire body and its extreme distal end or tip 14, respectively, of lead 10. Referring to FIGS. 1, 1A, and 1B collectively and in which like reference numerals are used to refer to like structures, guidewire 10 comprises, in this embodiment, two interwound filars 16, 18. Bi-, tri-, and quadrifilar (or more) structures would be useable in this invention. As is best seen in FIGS. 1A and 1B, the filars are interwound through most of the length of the guidewire body but become unifilar toward the distal end of the device. Also to be noted is the fact that the filars 16 and 18 have different diameters "d" and "d1". The filars of this version of a bifilar guidewire-based temporary pacing lead of this invention have different diameters to provide a slightly radially outwardly displaced exposed metal surface (e.g., 22 in FIG. 1.*b*, and further described below) on one of the filars to couple to a ring or other electrode means or contact means structure.

It will be understood that filars 16 and 18 are coated with insulative coatings e.g., an insulative polyimide coating (e.g., the coatings aromatic polyimide and methods described in Minar et al., U.S. Pat. No. 7,627,382, "Medical Devices with Aromatic Polyimide Coatings," the disclosure of which is incorporated by reference herein) so that no electrical "shorts" are created between the filars or, for that matter, other conductive pathways within the body. The insulative coating 20, particularly of the larger diameter filar, is best shown in FIG. 1B.

In FIG. 1B insulative coating 20 is shown to be partially removed (at 22) from several helices of coil 16. Removal of insulative coating 20 from filar 16 exposes conductive bare metal on at least the outer portion of the insulation-removed helix 24. As is noted above, the exposed bare metal portion is slightly radially outwardly located or disposed so that an electrically coupled electrode structure or contact means (e.g., 26 but not shown in FIG. 1.B.) can be coupled thereto. That bare metal portion of the helix then is electrically coupled to a sizeable electrode structure such as the ring structure 26 in FIG. 1. Further, insulated smaller diameter filar coils 18 are electrically coupled to tip structure 28, thereby providing a second electrical pathway which is insulated from the pathway provided by larger diameter coil 16 and ring-shaped electrode structure 26. In this manner the required separate insulated electrical pathways are provided which can then be used for cardiac pacing, sensing and other lead functions.

It is to be noted that utilization of a "pig-tail" electrode structure provides one of many possible means to bias electrode structure 26 toward surrounding tissue. The loop of the pig tail structure is collapsed e.g., in an arterial or venous lumen, so that an outward force is imparted against electrode structure 26. Biasing electrode structure 26 toward surrounding tissue maintains the required electrical contact to permit pacing, sensing, etc., (sometimes referred to as "capture") during coronary medical procedures and recovery. Note that many cardiac procedures are performed on a beating heart. Such a biasing structure, or its equivalent, is clearly needed for such procedures.

Alternatively, or concurrently, electrode structure 28 and its supporting distal guidewire connection may be modified to enhance capture. For example distal tip 14 may be curved, "J"-shaped, or otherwise modified to create and maintain the electrical contact needed for pacing/sensing to be accomplished. To provide this biasing structure the filar structures themselves may be imparted with a disposition to coil or "memory" as is well-known in the coil winding art. In this embodiment, the diameter of the pig-tail is about 1 inch. The diameter of the pig-tail will to a large extent determine the electrical separation distance between pacing and return electrode structures 26 and 28 in the coronary or peripheral vasculature.

Figure 2:
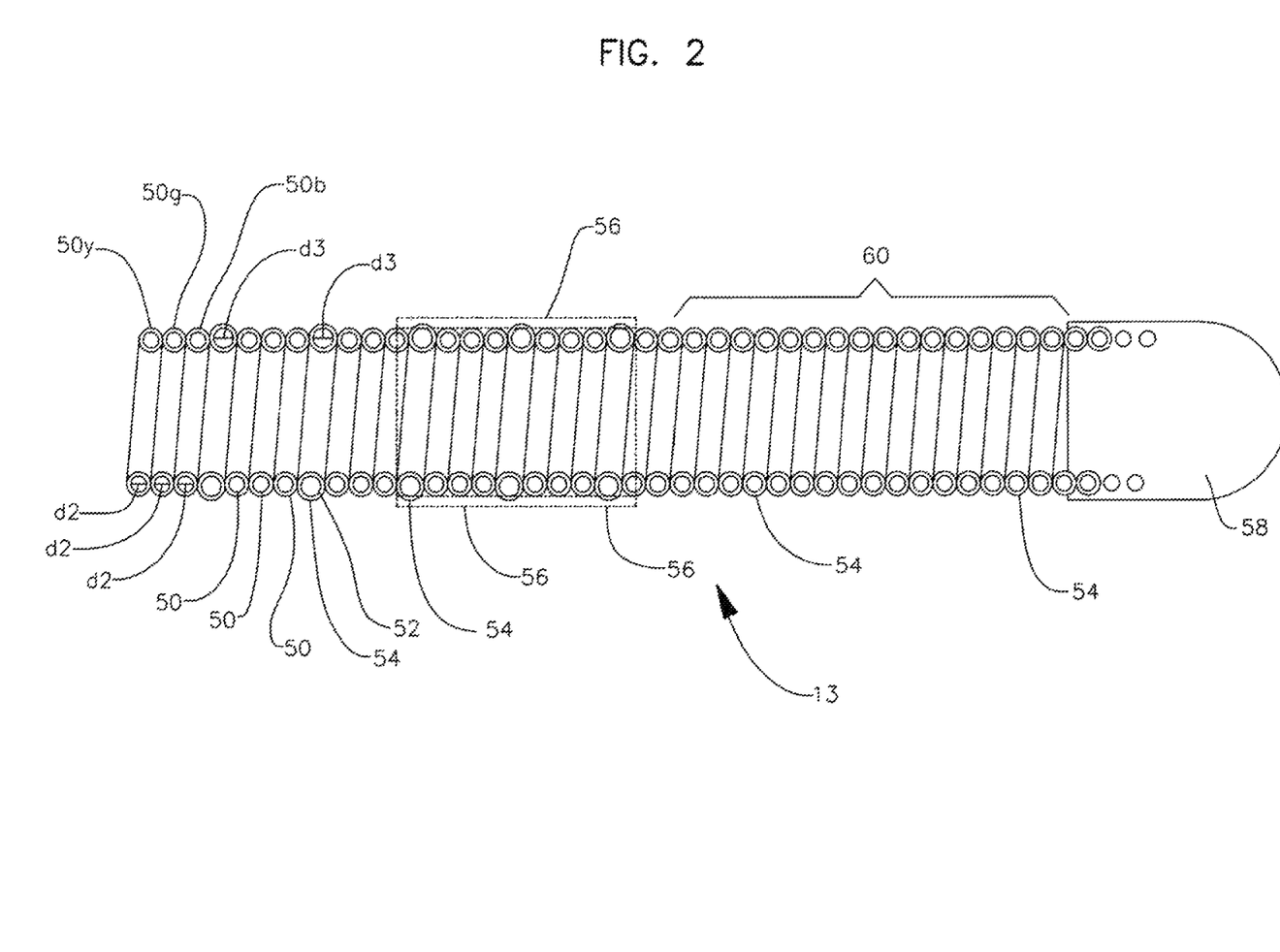
FIG. 2 illustrates in section a quadrifilar version of the present invention.

FIG. 2 illustrates in section a quadrifilar version 13 of the present invention. In this embodiment three of the four filars 50 have one wire diameter "d2" while the fourth filar 52 has a wire diameter "d3". Filars 50, 52 all have an electrically insulative coating or layer 54 thereon to prevent intra-filar and intra-electrode electrical shorting. (Insulative layer 54 has been partially removed from larger wire diameter filar 52 to expose the underlying conductive bare filar metal which, in turn, is electrically coupled to ring electrode structure 56 (shown in phantom). As in the structure above, the guidewire body is multifilar throughout most, if not the majority, of its length and becomes unifilar immediately proximal to its atraumatic distal tip/electrode contact or electrical means at bracket 60. Analogously, smaller wire diameter filars 50 are electrically coupled to the guidewire tip 58 which is the second conductive pathway required for pacing/sensing. That structural aspect of this embodiment of the invention is the same as the embodiment shown in FIG. 1. One skilled in this art will recognize that the selection of number of filars and coupling of same to pacing/sensing electrode structures will have many possible coil and electrode/contact/contact means combinations. Moreover, different combinations of the number of filars coupled to an electrode could be used. For example, in a quadrifilar construction, three filars could be coupled to one electrode surface, contact or electrode means and the fourth coupled to a second electrode surface or electrode means.

One skilled in this art also will appreciate that insulative coating or layer 54 could be given different colors, primarily for increased safety in assembling and using the lead. For example, filars 50 could be individually coated with different insulation colors such as yellow (50*y*), green (50*g*), or blue (50*b*) while filar 52 e.g., 52*r*) would be insulatively coated with a material of a different color, e.g., red.

Figure 3A:
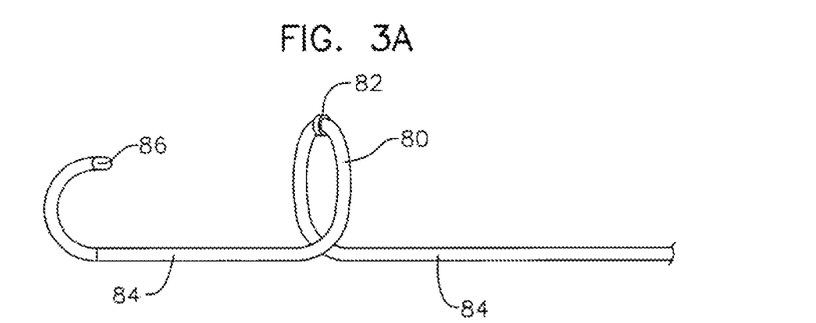
FIGS. 3A and 3B illustrate schematically an embodiment of this invention in which a loop is employed to provide an electrode biasing structure or biasing means.
Figure 3B:
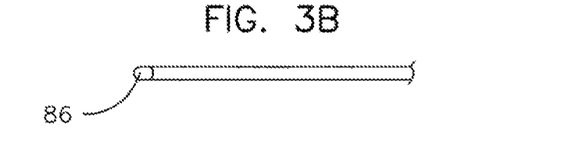

FIG. 3, in variations A. and B., illustrates schematically an embodiment of this invention in which a loop 80 is employed to provide a biasing structure or biasing means to urge ring-shaped electrode 82 into and to maintain contact with adjacent tissue. Guidewire body 84 is at least bifilar to provide the requisite conductive pathways to ring electrode 82 and tip electrode structure 86. Cold-working, hot-working and other conventional techniques are used to impart loop structure 80 to guidewire body 84. FIG. 3 B. is a straight version of this embodiment of this invention.

Figure 4:
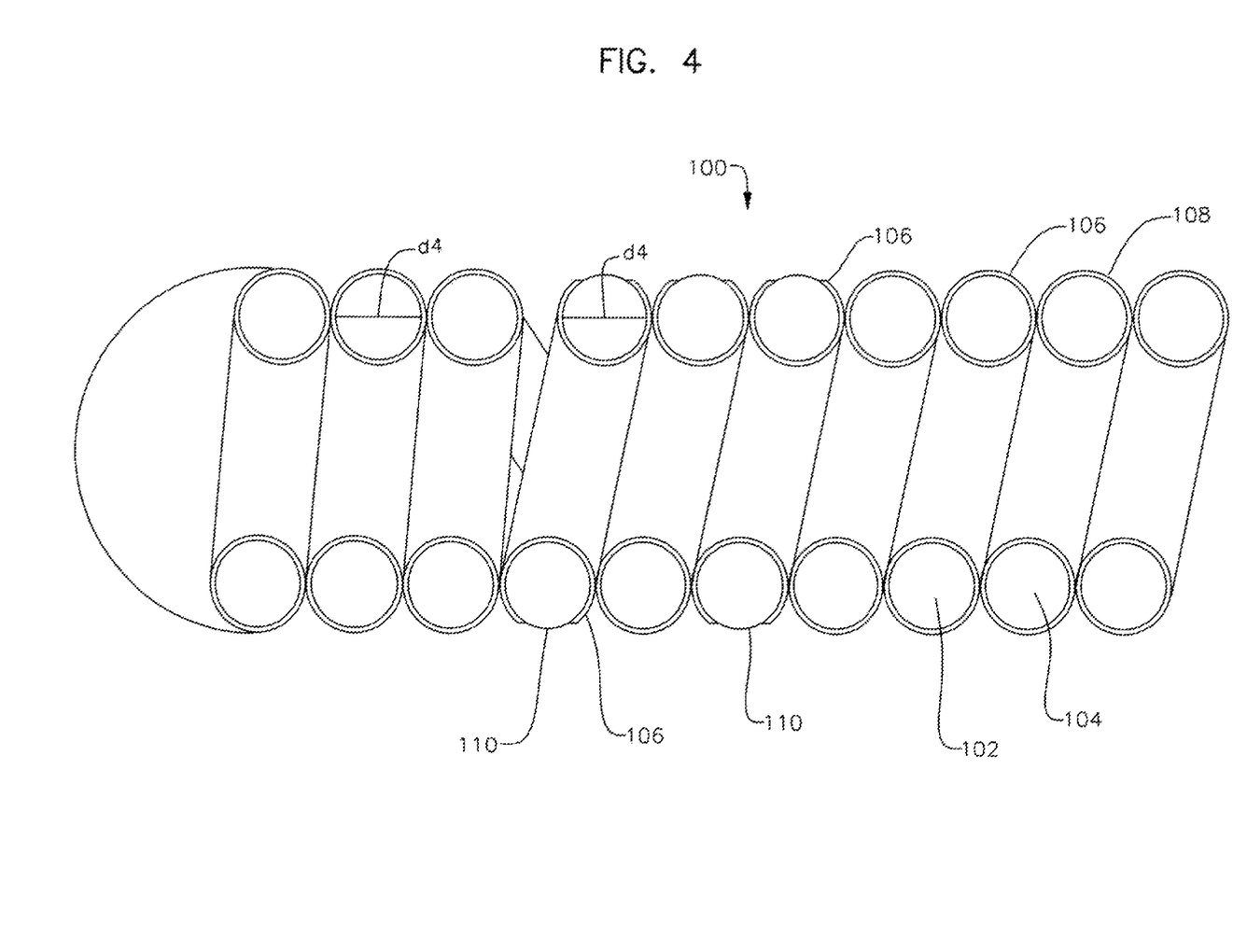
FIG. 4 is a bifilar version of the present guidewire-based pacing lead in which the filar wire diameters are the same.

FIG. 4 is a further bifilar 102, 104 version of the present guidewire-based pacing lead 100 in which the filar wire diameters d4 are the same. As with earlier versions of this invention, filars 102, 104 have insulative coating 106,108 (which may, of course, be the same insulative material) thereon. As is shown in greater detail insulative coating 106 has been at least partially ablated (removed, e.g., by laser etch) from the outside of filar 102 to expose conductive bare filar metal (at 110). Exposed conductive filar metal can be coupled to further conductive structures or means (e.g., electrode means or contact means) such as the ring structure noted above (not shown in this figure) to provide one of the electrical pathways for pacing/sensing. It is, of course, within the contemplation of this invention that there be no separate electrode structure and the bare metal exposed surface of the filar becomes the contact, contact means, electrode or electrode means.

Figure 5:
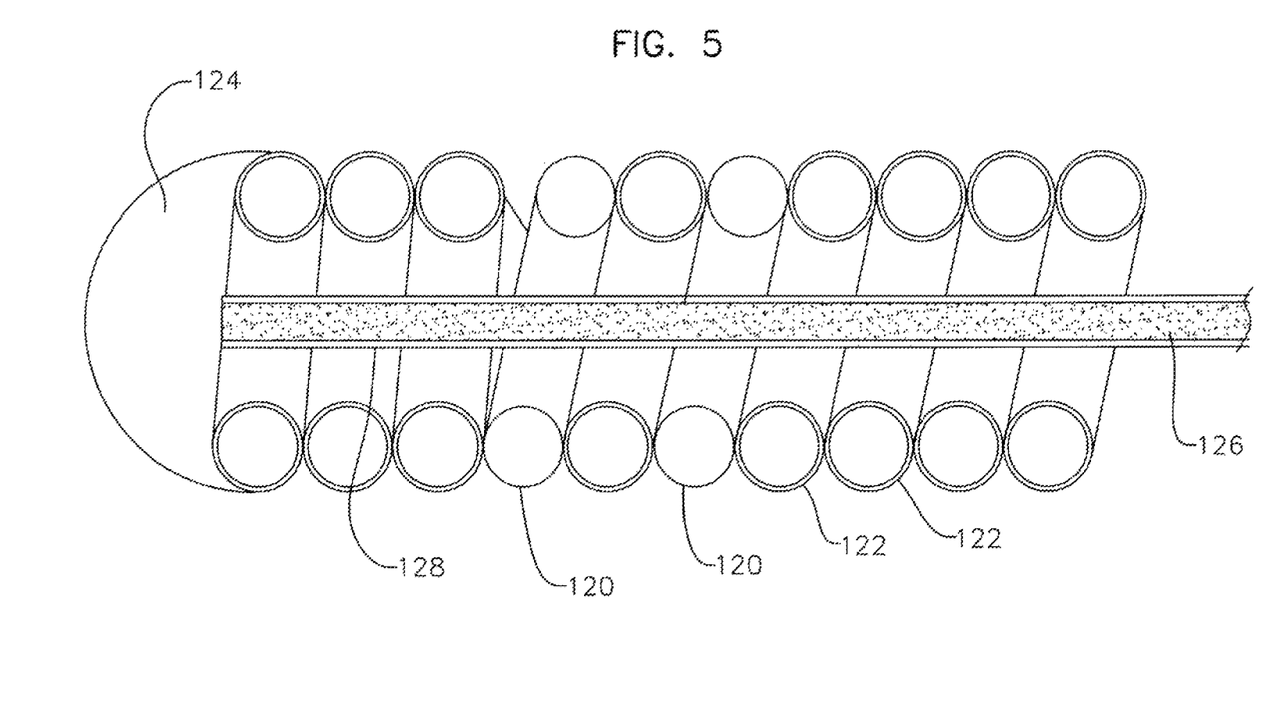
FIG. 5 is a variation of this invention in which insulative material has been removed from one of the filars.

A variation of this invention in which all of the insulative material has been removed from one of the filars is shown in FIG. 5. The non-insulated (i.e., bare metal) filars 120 and insulated filars 122 comprise the guidewire body to its distal tip (which is all that is shown in FIG. 5). In this version, the second conductive pathway needed for pacing/sensing is provided by the extreme distal tip 124 which is electrically coupled to guidewire core wire 126. Guidewire core wire 126 itself has an electrically insulative layer 128 thereon. One skilled in this art will appreciate that the entire guidewire structure may, in fact, be immersed in fairly conductive bodily fluids when in use. Thus, the actual combination of structures chosen to provide the requisite conductive pathways may be largely determined by the intended use for the lead.

Figure 6:
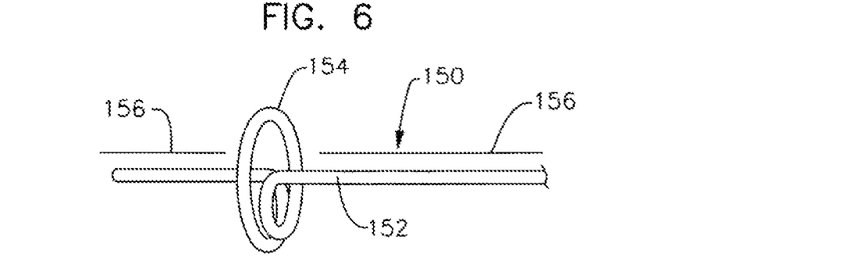
FIGS. 6 and 7 show straight and "J"-tipped versions of this invention.
Figure 7:
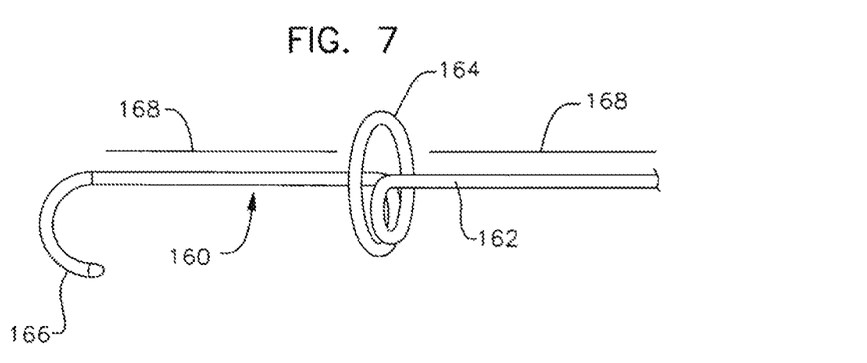

FIGS. 6 and 7 show straight 150, and "J"-tipped 160,166 versions of this invention in which a segment of the guidewire body 152, 162 has been formed into a 360°, circular structure 154, 164 which provides one of the electrically conductive pathways, i.e., the electrode is a "target" structure comprising segments of exposed bare metal guidewire filar. The insulated filars which comprise loops 154 and 164 may be ablated on their exterior exposed surfaces, within the loops themselves, or ablated to be completely bare. In summary, the circular electrode lies roughly in a plane which is perpendicular to the axis 156, 168 of the guidewire/lead body 152, 162.

Figure 8:
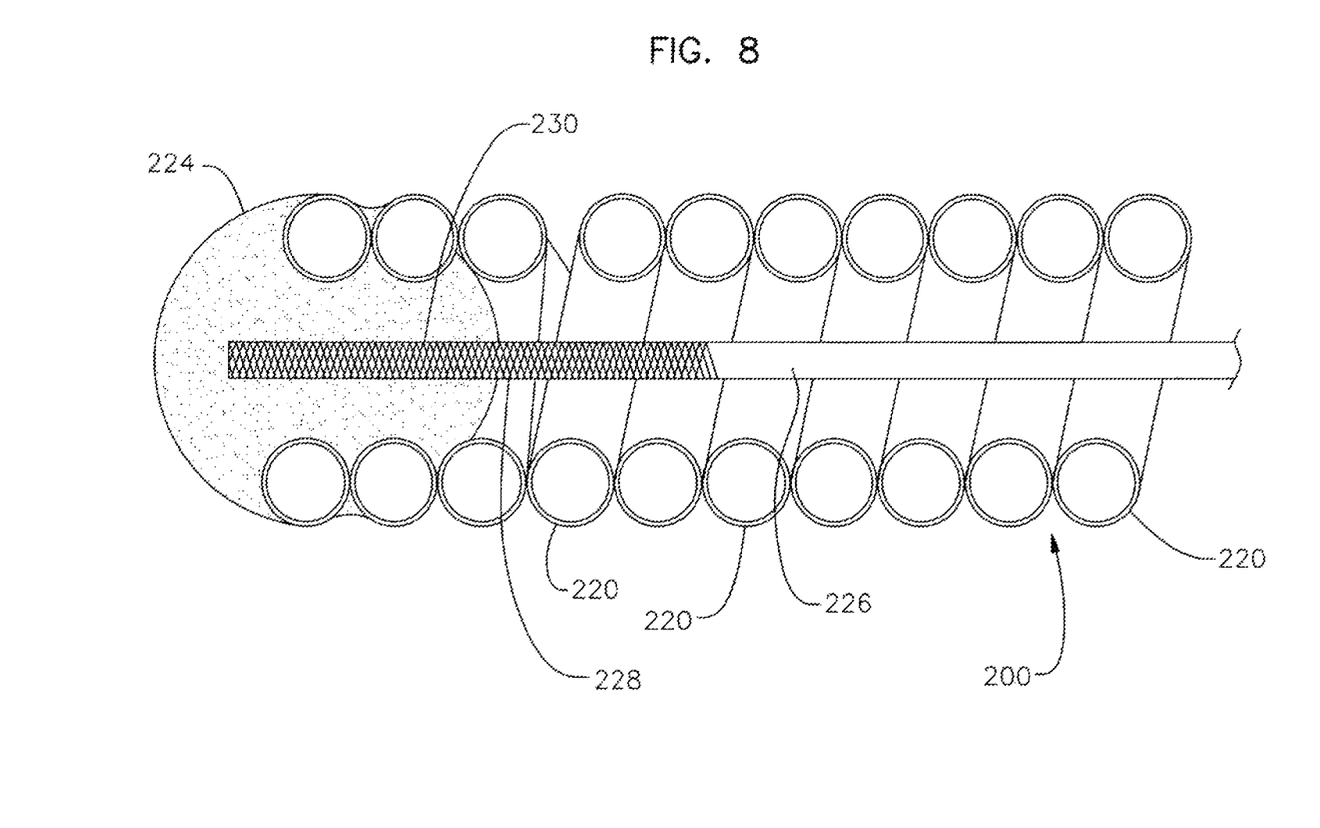
FIG. 8 illustrates a variation of the present invention analogous to the structure shown in FIG. 5 except that an insulated woven core structure is used.

FIG. 8 is a variation of the guidewire/lead 200 of present invention analogous to the structure shown in FIG. 5 except that instead of having an insulated core wire 126 as in FIG. 5, an insulated woven core structure 226 is used. Using this embodiment additional tip flexibility and steerability may be obtained. The tip, as in the other embodiments may be straight or "J"-shape (not shown). Tip 224 is machined to cooperate with the insulated layer 228 braided core structure, an adhesive 230 being used to couple the two structures 224, 230.

Figure 9:
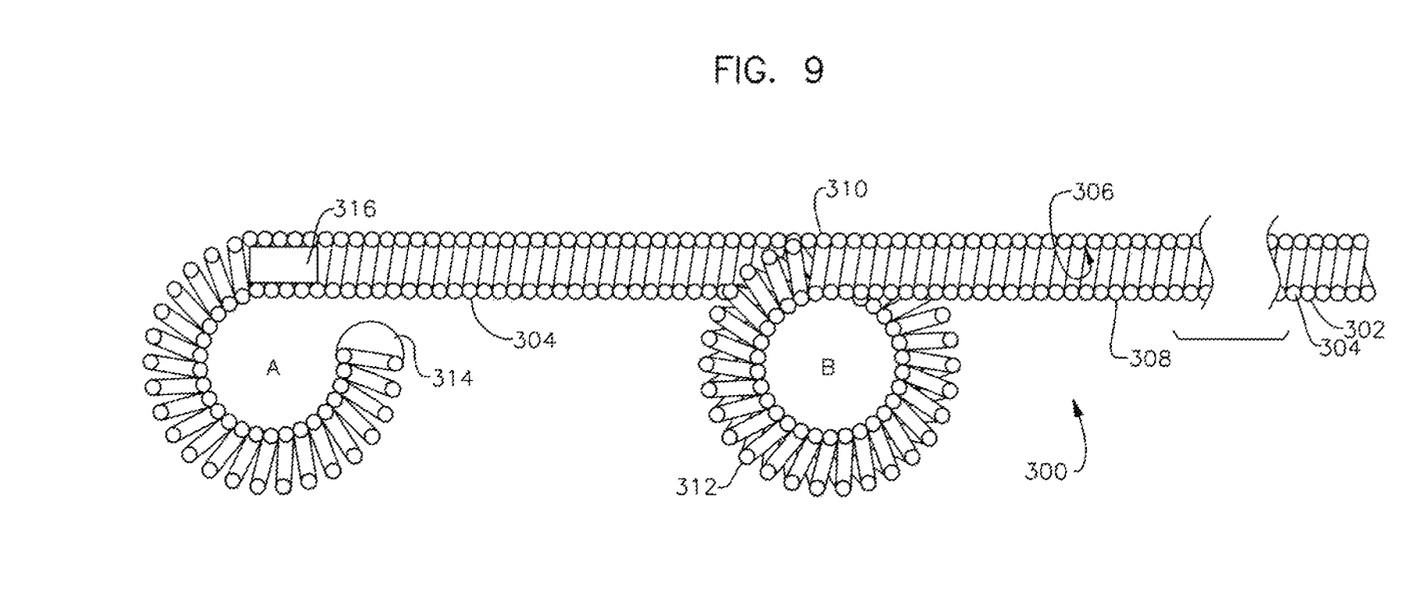
FIG. 9 illustrates a bifilar pacing/sensing lead guidewire-styled embodiment of the present invention in which interwound filars define the guidewire/lead body.

FIG. 9 illustrates a bifilar pacing/sensing lead guidewire-styled embodiment of the present invention 300 in which interwound filars 302, 304 comprise and define the guidewire/lead body, and, also define a potentially useful lumen 306. From the proximal end or portion of the lead 308 to about the turn or helix designated 310, the lead body is bifilar. At about the turn 310 the bifilar coil wind separates and becomes unifilar (monofilar) to and through the rest (primarily the distal end or segment) of the lead. Separated filar 302 then provides structure, e.g., bare wire, insulated, ablated wire at 312, as discussed above which is usable to provide a first electrode means "B". The remaining filar 304 provides the conductive pathway to a tip electrode means "A", e.g., a bulbous atraumatic tip 314. An optional insulative silicone plug 316 is inserted into the distal end of lumen 306 to seal it.

Figure 10:
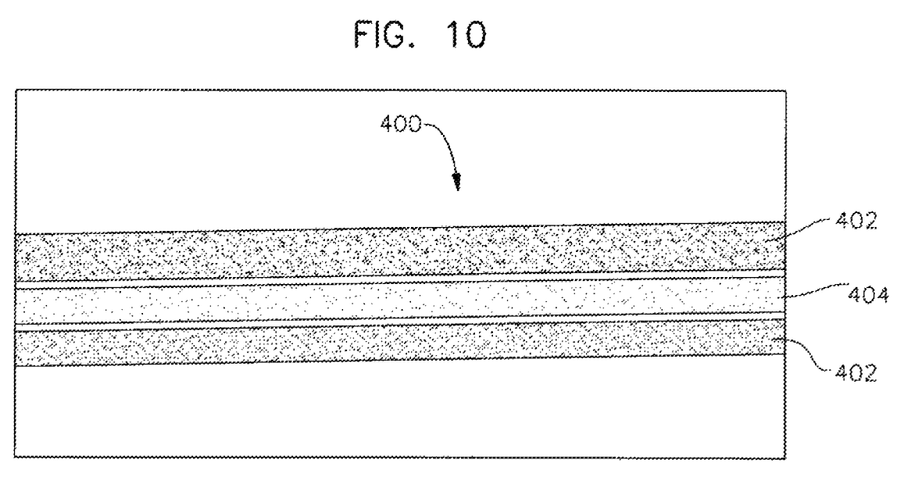
FIG. 10 is a line drawing of an insulatively coated filar of the present invention showing a partially laser-ablated insulative coating.

FIG. 10 is a line drawing of an insulatively coated filar 400 of the present invention showing a partially laser-ablated insulative coating 402 and the exposed, conductive bare metal 404 therebeneath.

Generally speaking, conventional guidewire-sized dimensions and guidewire materials will be used to produce this lead. Outside diameter of a device of this invention will in the usual case be 0.035 in. Larger and smaller diameters may be used. 304 stainless steel filar or coil wire with a polyimide insulative coating has been found to be particularly advantageous. Other insulative coatings, e.g., fluroimide, are contemplated. Generally, filar diameters (e.g., d, d1, d2, d3, and d4) will be in the 0.006 to 0.007 inch range. Insulative coatings should be as thin as possible to reduce overall lead diameter. Polyimide coatings as thin as 0.001 in. are preferred, the minimum thickness being dictated by the required electrical insulative properties and elimination of electrical "cross talk".

It is contemplated that the present guidewire-style pacing/sensing/defibrillation lead will have many short and longer term applications (acute and chronic) in many and various medical procedures. A specific application is that of either or both of mitral or aortic valvuloplasty such as that described by Hara et al., "Percutaneous Balloon Aortic Valvuloplasty Revisited: Time for a Renaissance?" *Circulation* 2007; 115: e334-e338, the teaching of which is incorporated by reference herein (including the references cited therein). A lead of this invention would be used e.g., to induce a rapid 220 bpm ventricular pacing to provide time for 3 balloon inflation valvuloplasty steps within the aortic valve as is described in the article. The clear advantage of use of the present invention is that the one steerable structure of this invention provides vascular access pacing, sensing and defibrillation capabilities without a need to utilize other steering, stiffening or straightening devices. In addition to reducing costs and EP lab time, smaller diameter devices permits treatment of smaller vascular structures in a larger size array of patients. Other references describing applications for which the present invention may be used (or for which the present invention may substitute) include:

Auth et al., Patent Application Publication US 2007/0088355, "Transseptal Left Atrial Access and Septal Closure";

Pedersen et al., Patent Application Publication US 2005/00075662, "Valvuloplasty Catheter";

Schwartz et al., Patent Application Publication US 2002/0098307, "Material Useable for Medical Balloons and Catheters";

Schwartz et al., Patent Application Publication US 2009/0018608, "Cardiac Stimulation Apparatus and Method for the Control of Hypertension"

Pedersen et al., Patent Application Publication US 2005/0090846, "Valvuloplasty Devices and Methods".

The teachings of these references (including the references cited therein) are incorporated by reference herein and are attached hereto as part of this application.

What is claimed is as follows:
1. An implantable lead, comprising:
 a) at least a first electrically conductive filar helically interwound along a longitudinal axis in a side-by-side rela- tionship with a second electrically conductive filar, the first and second filars provided with an electrically insulative coating, b) wherein the first filar has a first filar diameter and the second filar has a second filar diameter, the first filar diameter being greater than the second filar diameter, and wherein the first filar of the greater first filar diameter has at least a portion of its insulative coating removed at or adjacent to a distal first filar end to thereby provide exposed surfaces of the first electrically conductive filar facing outwardly, away from the longitudinal axis;

c) a ring-shaped electrode comprising a ring sidewall having an inner ring surface extending along the longitudinal axis for a ring length, wherein the inner ring surface is in electrical contact with the outwardly facing exposed surfaces of the first electrically conductive filar, and wherein a first proximal connector means is electrically connected to a proximal first filar end; and d) a second distal contact means electrically connected to a distal end of the second filar, wherein the second distal contact means is configured for at least one of stimulation and sensing of tissue, and a second proximal connector means electrically connected to a proximal end of the second filar, e) wherein the first and second connector means are configured for electrically connecting the lead to an electronic device.

2. The lead according to claim 1 wherein the ring-shaped electrode resides at an outwardly-biased circular structure defined by the lead.

3. The lead according to claim 1 wherein the lead defines a loop, and the ring-shaped electrode resides in the loop.

4. The lead according to claim 1 wherein the outwardly facing exposed surfaces of the first electrically conductive filar face outwardly, away from the longitudinal axis, for an exposed conductive filar length that is less than the ring length of the ring sidewall.

5. The lead according to claim 1 wherein the first ring-shaped electrode and the second distal contact means are sufficiently spaced-apart so that an electrical short pathway is not presented therebetween when both the ring-shaped electrode and the second distal contact means are applied to tissue.

6. The lead according to claim 1 wherein the first and second helically interwound electrically conductive filers define a lumen.

7. The lead according to claim 1 wherein the first and second filars are interwound in the side-by-side relationship extending to the ring-shaped electrode where the first filar ends with the second filar continuing to a tip electrode serving as the second distal contact means.

8. The leads according to claim 7 wherein the first and second interwound filars define a lumen extending to the ring-shaped electrode where the first filar ends and where the lumen continues, extending distally, now being formed by the second helically wound filar.

9. The leads according to claim 8 wherein a plug is supported in the lumen, the plug being proximal the tip electrode.

10. The lead according to claim 1 wherein the first and second filar diameters range from 0.006 to 0.007 inches.

11. The lead according to claim 1 wherein the insulative coating is polyimide or fluoroimide.

12. The lead according to claim 1 wherein the insulative coating has a thickness of 0.001 inches.

13. The lead of claim 1 wherein the first and second filars are of stainless steel.

14. The lead of claim 1 wherein the lead has an outside diameter of 0.035 inches.

15. An implantable lead, comprising:

a) at least a first electrically conductive filar helically interwound along a longitudinal axis in a side-by-side relationship with a second electrically conductive filar to thereby define a lumen, the first and second filars provided with an electrically insulative coating, b) wherein the first filar has a first filar diameter and the second filar has a second filar diameter, the first filar diameter being greater than the second filar diameter, and wherein the first filar of the greater first filar diameter has at least a portion of its insulative coating removed at or adjacent to a first distal end thereof to thereby provide exposed surfaces of the first electrically conductive filar facing outwardly, away from the longitudinal axis;

c) a ring-shaped electrode comprising a ring sidewall having an inner ring surface extending along the longitudinal axis for a ring length, wherein the inner ring surface is in electrical contact with the outwardly facing exposed surfaces of the first electrically conductive filar, and wherein a first proximal connector means is electrically connected to a proximal end of the first filar; and d) an insulated core wire disposed within the lumen defined by the helically interwound first and second filars, wherein a distal end of the core wire is electrically connected to a tip electrode, and wherein a second proximal connector means is electrically connected to a proximal end of the core wire, e) wherein the first and second connector means are configured for electrically connecting the lead to an electronic device.

16. The lead according to claim 15 wherein the outwardly facing exposed surfaces of the first electrically conductive filar face outwardly, away from the longitudinal axis, for an exposed conductive filar length that is less than the ring length of the ring sidewall.

17. The lead according to claim 15 wherein the first ring-shaped electrode and the tip electrode are sufficiently spaced-apart so that an electrical short pathway is not presented therebetween when both the ring-shaped electrode and the tip electrode are applied to tissue.

18. An implantable lead, comprising:

a) at least a first, second, third and fourth electrically conductive filars helically interwound along a longitudinal axis, the first, second, third and fourth filars being provided with an electrically insulative coating, b) wherein the first, second, third and fourth filars have respective first, second, third and fourth filar diameters, the first filar diameter being greater than the second, third and fourth filar diameters, and wherein the first filar of the greater first filar diameter has at least a portion of its insulative coating removed at or adjacent to a first distal end thereof to thereby provide exposed surfaces of the first electrically conductive filar facing outwardly, away from the longitudinal axis;

c) a ring-shaped electrode comprising a ring sidewall having an inner ring surface extending along the longitudinal axis for a ring length, wherein the inner ring surface is in electrical contact with the outwardly facing exposed surfaces of the first electrically conductive filar, and wherein a first proximal connector means is electrically connected to a proximal end of the first filar; and d) a second distal contact means electrically connected to a distal end of at least the fourth filar, wherein the second distal contact means is configured for at least one of stimulation and sensing of tissue, and a second proximal connector means electrically connected to a proximal end of the fourth filar, e) wherein the first and second connector means are configured for electrically connecting the lead to an electronic device.

19. The lead according to claim 18 wherein the second and third filars have the greater first filar diameter, and wherein the second and third filars of the greater first filar diameter have at least a portion of their insulative coating removed at or adjacent to respective second and third distal ends thereof to thereby provide exposed surfaces of the first, second and third electrically conductive filars facing outwardly, away from the longitudinal axis, and wherein the inner ring surface is in electrical contact with the outwardly facing exposed surfaces of the first, second and third electrically conductive filars, and wherein the first proximal connector means is electrically connected to a proximal end of the first, second and third filars.

20. The lead according to claim 18 wherein the first, second, third and fourth interwound filars define a lumen extending to the ring-shaped electrode where the first, second and third filar end and where the lumen continues, extending distally, now being formed by at least the fourth helically wound filar.

21. An implantable lead, comprising:
   a) at least a first electrically conductive filar helically interwound along a longitudinal axis in a side-by-side relationship with a second electrically conductive filar, the first and second filars provided with an electrically insulative coating,
   b) wherein the first filar has a first filar diameter extending from a proximal first filar end to a distal first filar end and the second filar has a second filar diameter extending from a proximal second filar end to a distal second filar end, the first filar diameter being greater than the second filar diameter, and wherein the first filar of the greater first filar diameter has at least a portion of its insulative coating removed at or adjacent to the distal first filar end to thereby provide exposed surfaces of the first electrically conductive filar facing outwardly, away from the longitudinal axis;
   c) a ring-shaped electrode comprising a ring sidewall having an inner ring surface extending along the longitudinal axis for a ring length, wherein the inner ring surface is in electrical contact with the outwardly facing exposed surfaces of the first electrically conductive filar, and wherein a first proximal connector means is electrically connected to the proximal first filar end; and
   d) a second distal contact means electrically connected to a distal end of the second filar, wherein the second distal contact means is configured for at least one of stimulation and sensing of tissue, and a second proximal connector means electrically connected to a proximal end of the second filar,
   e) wherein the first and second interwound filars define a lumen extending to the ring-shaped electrode where the first filar ends and where the lumen continues, extending distally, now being formed by the second helically wound filar, and wherein a plug is supported in the lumen, the plug being proximal the second distal contact means, and
   f) wherein the first and second connector means are configured for electrically connecting the lead to an electronic device.

\* \* \* \* \*